United States Patent [19]

Pauling

[11] 4,421,749

[45] Dec. 20, 1983

[54] ALUMINUM PYRIDINETHIOLS AS ANTIMICROBIALS

[75] Inventor: Horst Pauling, Bottmingen, Switzerland

[73] Assignee: Hoffmann-La Roche Inc., Nutley, N.J.

[21] Appl. No.: 277,781

[22] Filed: Jun. 26, 1981

[30] Foreign Application Priority Data

Jul. 2, 1980 [CH] Switzerland ................ 5112/80

[51] Int. Cl.³ ............... A61K 31/555; C07D 213/89
[52] U.S. Cl. .................... 424/200; 424/DIG. 4; 424/245; 546/6; 252/106
[58] Field of Search ........... 424/DIG. 4, 68; 546/6

[56] References Cited

U.S. PATENT DOCUMENTS

| | | | |
|---|---|---|---|
| 3,347,863 | 10/1967 | Ottmann | 424/31 |
| 3,953,450 | 4/1976 | Bouillon | 546/6 |
| 4,055,634 | 10/1977 | Brenner et al. | 424/68 |
| 4,072,742 | 2/1978 | Bouillon et al. | 546/6 |
| 4,209,506 | 6/1980 | Bouillon et al. | 546/6 |
| 4,275,199 | 6/1981 | Bouillon | 546/6 |

Primary Examiner—Mark L. Berch
Attorney, Agent, or Firm—Jon S. Saxe; George M. Gould; John J. Maitner

[57] ABSTRACT

Organoaluminum compounds of the formula

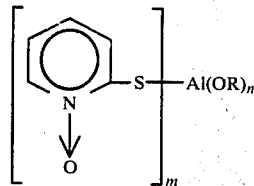

wherein m, n and R are as defined hereinafter, and processes for their preparation are disclosed. The compounds of formula I possess antimicrobial properties and are useful in cosmetic compositions, such as hair-care compositions and foot-care compositions.

18 Claims, No Drawings

ALUMINUM PYRIDINETHIOLS AS ANTIMICROBIALS

DETAILED DESCRIPTION OF THE INVENTION

This invention is directed to organoaluminum compounds of the formula

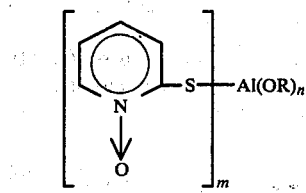
I wherein
m is 1 or 2,
n is 1 or 2,
whereby the sum m+n is 3, and
R is straight-chain $C_{1-22}$-alkyl; straight-chain or branched $C_{1-4}$-alkyl monosubstituted with phenoxy; 2,4-hexadienoyl; unsubstituted phenyl or phenyl substituted with 1 to 5 chlorine atoms or a phenyl group; or a group of the formula

(a)

wherein
$R^1$ is $C_{1-6}$-alkyl or,
where m is 1 and n is 2, the two R-symbols together form a 2,2'-methylene-bis(3,4,6-trichloro-o-phenylene) group of the formula

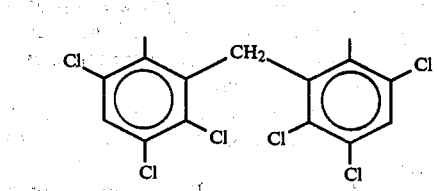
(b)

or, where m is 2 and n is 1, R is a 2,4,5-trichloro-6-[2,3,5-trichloro-6-[di(2-pyridinethiolato)aluminum]oxy-benzyl]phenyl N,N'-dioxide group of the formula

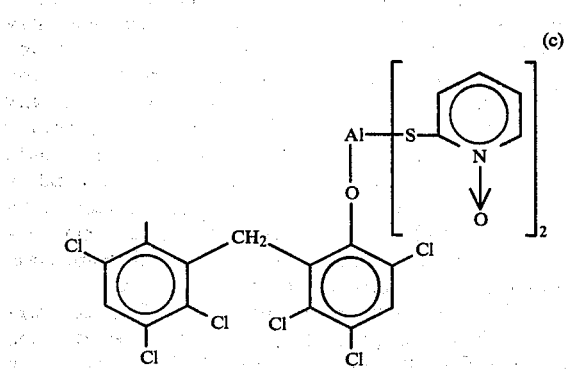
(c)

In formula I the R-symbols can be the same or different.

Examples of R as straight-chain $C_{1-22}$-alkyl are methyl, ethyl, n-propyl, n-butyl, n-pentyl, n-hexyl, n-octyl, n-decyl, n-hexadecyl, n-octadecyl and n-docosyl.

If R is a straight-chain $C_{1-22}$-alkyl, then this is preferably ethyl or n-hexadecyl.

If R is a straight-chain or branched $C_{1-4}$-alkyl monosubstituted with phenoxy, then this is preferably 2-phenoxyethyl.

If R is 2,4-hexadienoyl, then this is preferably trans, trans-2,4-hexadienoyl, i.e. sorbato.

If R is phenyl substituted with 1 to 5 chlorine atoms, then this is preferably 2,4,6-trichlorophenyl or phentachlorophenyl. If R is phenyl substituted with a phenyl group, then this is preferably o-phenylphenyl.

$R^1$ in the group of formula (a) can be straight-chain or branched alkyl, but straight-chain alkyl is preferred. Preferably, $R^1$ signifies ethyl.

Preferred compounds of formula I are those wherein m is 2, n is 1 and R is straight-chain or branched $C_{1-4}$-alkyl monosubstituted with phenoxy, 2,4-hexadienoyl, optionally substituted phenyl, as defined above, a group of formula (a) or the 2,4,5-trichloro-6-[2,3,5-trichloro-6-[di(2-pyridinethiolato)aluminum]oxy-benzyl]phenyl N,N'-dioxide group.

Especially preferred compounds are:
(2-Phenoxyethoxy)bis(2-pyridinethiolato)aluminum N,N'-dioxide,
bis(ethylphosphonato)(2-pyridinethiolato)aluminum N-oxide,
(sorbato)bis(2-pyridinethiolato)aluminum N,N'-dioxide,
(2-biphenylyloxy)bis(2-pyridinethiolato)aluminum N,N'-dioxide,
(ethylphosphonato)bis(2-pyridinethiolato)aluminum N,N'-dioxide and
[methylene-bis(3,4,6-trichloro-o-phenyleneoxy)]bis[(di-2-pyridinethiolato)]aluminum N,N', N'',N'''-tetroxide.

In certain of the compounds of formula I, there are present asymmetric carbon atoms and, accordingly, such compounds can be present as optical antipodes. Because of the presence of the double bonds in the compounds of formula I wherein R signifies 2,4-hexadienoyl, those compounds also exhibit geometric isomerism. Formula I is accordingly intended to include all of these possible isomeric forms.

The organoaluminum compounds of formula I are prepared by one of the procedures described hereinafter.

PROCEDURE A

Reacting a compound of the formula $(R^2)_3Al$  II wherein $R^2$ is a saturated, straight-chain or branched $C_{2-6}$-hydrocarbon group, with a compound of the formula

ROH  III wherein R is as described above, and with pyridine-N-oxide-2-thiol.

In accordance with Procedure A, the reaction can be carried out in one step or two steps. The following reaction equations represent the two possibilities (A)(i) and (A)(ii):

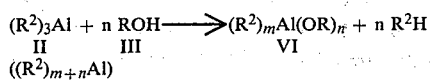  (A) (i)

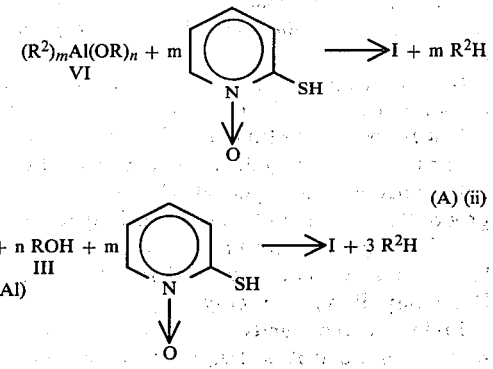

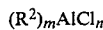  (A) (ii)

In the case of procedure (A)(i) (first step) or (ii), the reaction can be conveniently carried out by reacting the respective starting materials of formulae II and III, and in the case of process variant (A)(ii) also the pyridine-N-oxide-2-thiol starting material, in an inert organic solvent. Examples of suitable solvents are straight-chain or branched saturated aliphatic hydrocarbons, such as n-hexane and isooctane, optionally substituted aromatic hydrocarbons, such as benzene and toluene, halogenated hydrocarbons, such as methylene chloride and chloroform, and ethers or ether-like compounds, such as diethyl ether, dioxan and anisole. Since the starting materials of formulae II and III and the intermediates of formula VI are very susceptible to hydrolysis and these compounds as well as pyridine-N-oxide-2-thiol are also susceptible to oxidation, the reaction must be carried out under conditions which are as far as possible anhydrous and free of air. Consequently, anhydrous solvents are used, and the reactions are conveniently carried out in a dry protective gas atmosphere, such as nitrogen or argon.

The reaction temperatures can vary over a range between $-20°$ C. and $100°$ C., preferably between $0°$ C. and $60°$ C.

In procedure (A)(i), both steps can be carried out under analogous reaction conditions, as mentioned above. Isolation of the product of the first step, i.e. the compound of formula VI, is, therefore, not necessary. The same solvent as used in the first step can be used in the second step with the addition of an additional amount thereof, if necessary. The second step of the reaction is initiated by introduction of the pyridine-N-oxide-2-thiol.

The amounts of starting materials used in procedure (A) are conveniently stoichiometric and the starting materials themselves are preferably used in a condition which is as pure as possible. Under such circumstances, and since the reactions usually proceed completely quantitatively and the only by-product is the readily volatile lower hydrocarbon $R^2H$, the end product is normally obtained in high purity and, after removal of the solvent, for example, by evaporation, normally does not require additional purification.

Procedure B

Reacting a compound of the formula $(R^2)_mAlCl_n$  IV wherein $R^2$, m and n have the significance given above, with a compound of the formula $RO^{\ominus}Y^{\oplus}$  V wherein $Y^{\oplus}$ signifies an alkali metal (e.g. sodium or potassium) or an ammonium ion, and R has the significance given above, and with pyridine-N-oxide-2-thiol.

In the case of procedure B, the reaction is preferably carried out in two steps. The following reaction equations represent the two-step process:

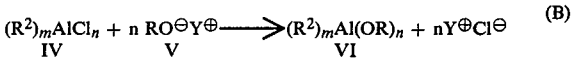  (B)

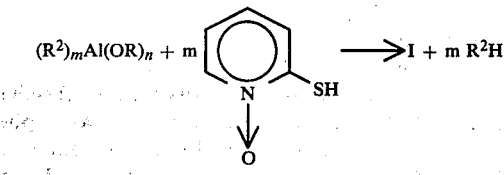

Suitable reaction conditions (e.g. solvent, exclusion of water, protective gas atmosphere, reaction temperatures and ratios of starting materials) are, in general, the reaction conditions mentioned above in relation to procedure A. In the case of porcedure B, the resulting precipitate of the salt of the formula $Y^{\oplus}Cl^{\ominus}$ is conveniently separated after completion of the first reaction step, e.g. by filtering the reaction mixture. The further procedure can be carried out as described for procedure A. Also in this case the reactions usually proceed completely quantitatively and, accordingly, purification of the end product is normally unnecessary.

The pyridine-N-oxide-2-thiol which is used in procedures A and B above cannot be stored indefinitely. For example, slow oxidation to the corresponding disulphide occurs in the air. For this reason, the free thiol is advantageously prepared freshly before each reaction from the stable and commercially available sodium thiolate by acidification.

The compounds of formulae II, III, IV and V which are used as starting materials are either known or can be prepared according to methods conventional in the art.

As in the case with many known aluminum compounds, the aluminum atom in the compounds of formula I can form, with the aid of so-called secondary valency bonds, spacial structures in which the aluminum atom has higher coordination numbers, for example, 4 or 6. The resulting complex structures usually have no uniform molecular weight, but are oligomers or polymers of the corresponding monomeric compounds. For this reason, the melting points of the compounds in question are generally not characteristic; in most cases the compounds have, on the other hand, a relatively narrowly limited melting range in which decomposition of the particular product frequently occurs.

The organoaluminum compounds of formula I possess antimicrobial properties, especially bactericidal and fungicidal properties. An example of a fungus strain against which the compounds of formula I are active is *Pityrosporum ovale*. This strain is mainly responsible for the formation of dandruff of the scalp. Among the bacteria strains against which the compounds of formula I are active are *Staphylococcus aureus, Escherichia coli, Pseudomonas aeruginosa* and *Mycobacterium tuberculosis*.

In view of their bactericidal and fungicidal activity, the compounds of formula I are especially suitable as active substances for cosmetic compositions, namely for hair-care compositions for the control or prevention of dandruff of the scalp, and foot-care compositions. For this purpose the compounds of formula I can be formulated in various compositions. The cosmetic compositions in accordance with the invention are characterised in that they contain an antimicrobially-effective amount of at least one compound of general formula I, as defined above, as well as conventional hair-care or foot-care carrier materials or other cosmetically-effective adjuvants. The compositions of this invention are, for example, shampoos, hair washes, setting compositions (setting gels), sprays and lotions. The compositions are preferably present in liquid form.

In the compositions in accordance with the invention, the concentrations of active substance of formula I generally amount to 0.001 to 5 weight percent, preferably 0.01 to 3 weight percent.

In compositions which are in the form of shampoos, the concentration of active substance of formula I is preferably from about 0.05 to 2, especially from 0.1 to 1, weight percent. The preferred concentrations in hair washes and setting compositions are from about 0–0.005 to 0.2, especially at about 0.01 to 0.1, weight percent. In the case of lotions, which are present in the form of aqueous solutions or, preferably, aqueous-alcoholic solutions, the concentration of active substance of formula I is preferably from about 0.01 to 0.1 weight percent. Sprays, which are normally formulated as alcoholic solutions with a carrier gas, preferably contain from 0.01 to 3, especially 0.05 to 2, weight percent of active substance of formula I based on the total weight of the aerosol mixture.

It will be appreciated that the individual embodiments of the cosmetic compositions in accordance with the present invention, such as shampoos, lotions or sprays, can contain conventional ingredients present in cosmetic formulations, such as detergents, preservatives, antioxidants, perfumes, and the like. In the lotions and sprays there can be used, for example, as the alcohols especially ethanol or isopropanol, with the aqueous-alcoholic solutions preferably containing 30 to 80 weight percent of alcohol. For sprays there can be used all conventional carrier gases which are customary in aerosol mixtures, for example, halogenated hydrocarbons.

The method in accordance with the invention for the control or prevention of dandruff of the scalp is characterized by treating the scalp with an effective amount of a hair-care composition in accordance with the invention.

On the basis of their fungicidal activity, the organoaluminum compounds of formula I can also be used in agriculture and in horticulture.

The following Examples further illustrate the present invention:

I. Manufacture of the active substances:

EXAMPLE 1

Ethoxy-bis(2-pyridinethiolato)aluminum N,N'-dioxide

A solution of 3.7 g of anhydrous ethanol in 50 ml of absolute toluene is added dropwise with stirring to a solution of 16 g of triisobutylaluminum in 100 ml of absolute toluene at 0° C. over a period of 1 hour. After completion of the addition, the reaction mixture is allowed to warm to room temperature and then warmed to 40° C. for about half an hour.

After cooling the so-obtained solution of ethoxydiisobutylaluminum, the solution is placed in the dropping funnel of a second apparatus with the exclusion of air and moisture by means of an inert gas. The flask of the first apparatus is rinsed with 20 ml of toluene and this is also added under an inert gas to the contents of the dropping funnel of the second apparatus.

20.5 g of freshly prepared pyridine-N-oxide-2-thiol are dissolved in 100 ml of absolute toluene at about 40° C. in the reaction flask of the second apparatus. This solution is cooled to 0° C., and the toluene solution of the ethoxydiisobutylaluminum prepared in the first step is added dropwise thereto over a period of about 2 hours while maintaining the temperaure at 0° C.; a yellow solution is obtained. After the addition is complete, the reaction mixture is allowed to stir for about 1 hour at 0° C., then 16 hours at room temperature and 1 hour at about 40° C. The reaction mixture is a light yellow colored suspension. The solvent is distilled off and the residue is extracted twice with 10 ml of n-hexane each time. The resulting white-yellow crystallizate is dried at 50° C. under a high vacuum to constant weight (about 12 hours) to yield 24.6 g (about 94.2% of theory) of ethoxy-bis(2-pyridinethiolato)aluminum N,N'-dioxide, m.p. 232°–235° C. with decomposition.

| Microanalysis | % C | % H | % N | % S |
|---|---|---|---|---|
| Calculated | 44.44 | 4.04 | 8.64 | 19.77 |
| Found | 44.06 | 3.98 | 8.49 | 19.89 |

EXAMPLE 2

(2-Biphenylyloxy)bis(2-pyridinethiolato)aluminum N,N'-dioxide

In a manner analogous to that described in Example 1, 16 g of triisobutylaluminum and 13.72 g of 2-phenylphenol are reacted in absolute toluene to afford (2-biphenylyloxy)diisobutylaluminum and this is then reacted with 20.52 g of pyridine-N-oxide-2-thiol to yield the title compound. The isolation of the product is carried out in an analogous manner. The yield of (2-biphenylyloxy)bis(2-pyridinethiolato)aluminum N,N'-dioxide, an almost white powder, is 33.4 g, about 92.5% of theory. Upon heating it sinters from about 174° C. and melts at 236°–238° C.

| Microanalysis | % C | % H | % N | % S |
|---|---|---|---|---|
| Calculated | 58.92 | 3.82 | 6.25 | 14.30 |
| Found | 58.98 | 3.91 | 6.22 | 14.34 |

EXAMPLE 3

(2,4,6-Trichlorophenoxy)bis(2-pyridinethiolato)-aluminum N,N'-dioxide

In a manner analogous to that described in Example 1, 17.5 g of triisobutylaluminum and 17.4 g of 2,4,6-trichlorophenol are reacted in absolute toluene to give (2,4,6-trichlorophenoxy)diisobutylaluminum and this is then reacted with 22.4 g of pyridine-N-oxide-2-thiol to afford the title compound. The isolation of the product is carried out in analogous manner. The yield of (2,4,6-trichlorophenoxy)bis(2-pyridinethiolato)-aluminum N,N'-dioxide, a fine white powder with a melting point of 207°-208° C., is 28.6 g, about 68% of theory.

| Microanalysis | % C | % H | % S | % N |
|---|---|---|---|---|
| Calculated | 40.4 | 2.12 | 13.48 | 5.89 |
| Found | 41.0 | 2.21 | 13.56 | 5.60 |

EXAMPLE 4

(1-Hexadecanolato)bis(2-pyridinethiolato)aluminum N,N'-dioxide

In a manner analogous to that described in Example 1, 16.0 g of triisobutylaluminum and 19.56 g of hexadecanol (cetyl alcohol) are reacted in absolute n-hexane to give (1-hexadecanolato)diisobutylaluminum and this is then reacted with 20.52 g of pyridine-N-oxide-2-thiol to give the title compound. The isolation of the product is carried out in an analogous manner. The yield of (1-hexadecanolato)bis(2-pyridinethiolato)aluminum N,N'-dioxide, a yellowish-grey white powder with a decomposition interval of 275°-280° C., is 36.1 g, about 86% of theory.

| Microanalysis | % C | % H | % N | % S |
|---|---|---|---|---|
| Calculated | 59.97 | 7.94 | 5.38 | 12.31 |
| Found | 59.72 | 8.10 | 5.44 | 12.30 |

EXAMPLE 5

[Methylene-bis(3,4,6-trichloro-o-phenyleneoxy)]-(2-pyridinethiolato)aluminum N-oxide To a solution of 8.96 g of freshly prepared pyridine-N-oxide-2-thiol and 28.5 g of hexachlorophene in 250 g of absolute diethyl ether at −10° C. is added dropwise a solution of 13.9 g of triisobutylaluminum in 30 ml of absolute n-hexane, a white precipitate forming. The reaction mixture is stirred for 16 hours at room temperature and thereafter for 1 hour at reflux temperature. Subsequently, the precipitate is filtered off, washed twice with a mixture of diethyl ether and n-hexane and dried for 4 hours in a high vacuum. The yield of [methylene-bis(3,4,6-trichloro-o-phenyleneoxy)]-(2-pyridinethiolato)aluminum N-oxide is 35.7 g, about 91.5% of the theoretical yield, of a white powder which melts at 228°-230° C. (with decomposition).

| Microanalysis | % C | % H | % N | % S |
|---|---|---|---|---|
| Calculated | 38.74 | 1.45 | 2.51 | 5.74 |
| Found | 38.99 | 1.45 | 2.58 | 6.08 |

EXAMPLE 6

[Methylene-bis(3,4,6-trichloro-o-phenyleneoxy)]-bis[-(di-2-pyridinethiolato)]aluminum N,N',N'',N'''-tetroxide In a manner analogous to that described in Example 5, 32.46 g of pyridine-N-oxide-2-thiol, 25.9 g of hexachlorophene and 25.2 g of triisobutylaluminum are reacted to give the title compound. The isolation of the product is carried out in an analogous manner. The yield of [methylene-bis(3,4,6-trichloro-o-phenyleneox-y)]-bis[(di-2-pyridinethiolato)]aluminum N,N',N'',N'''-tetroxide is 56.9 g, about 92.5% of theory, of a fine white powder with a melting interval of 208°-210° C.

| Microanalysis | % C | % H | % N | % S |
|---|---|---|---|---|
| Calculated | 41.14 | 2.09 | 5.82 | 13.31 |
| Found | 41.67 | 2.16 | 6.00 | 13.42 |

EXAMPLE 7

Bis(2-phenoxyethoxy)(2-pyridinethiolato)aluminum N-oxide

In a manner analogous to that described in Example 5, 16.23 g of pyridine-N-oxide-2-thiol, 35.2 g of 2-phenoxy-ethanol and 14.5 g of triethylaluminum are reacted to give the title compound. The isolation of the product is carried out in an analogous manner. The yield of bis(2-phenoxyethoxy)(2-pyridinethiolato)aluminum N-oxide is 50.9 g, about 93% of theory, of crystals with a melting point of 52°-55° C.

| Microanalysis | % C | % H | % N | % S |
|---|---|---|---|---|
| Calculated | 59.01 | 5.19 | 3.28 | 7.50 |
| Found | 59.40 | 5.25 | 3.07 | 7.51 |

EXAMPLE 8

(2-Phenoxyethoxy)bis(2-pyridinethiolato)aluminum N,N'-dioxide

In a manner analogous to that described in Example 5, 20.5 g of pyridine-N-oxide-2-thiol, 11.5 g of 2-phenoxy-ethanol and 22.8 g of trihexylaluminum are reacted to give the title compound. The isolation of the product is carried out in an analogous manner. The yield of (2-phenoxyethoxy)bis(2-pyridinethiolato)aluminum N,N'-dioxide is 31.3 g, about 93.1% of theory, of a fluffy whitish powder with a melting interval of 249°-252° C. (with decomposition).

| Microanalysis | % C | % H | % N | % S |
|---|---|---|---|---|
| Calculated | 51.92 | 4.11 | 6.73 | 15.40 |
| Found | 51.90 | 4.10 | 6.80 | 15.69 |

EXAMPLE 9

Diphenoxy(2-pyridinethiolato)aluminum N-oxide

In a manner analogous to that described in Example 1, 17.5 g of triisobutylaluminum and 16.6 g of phenol are reacted to give diphenoxyaluminum isopropoxylate and this is then reacted with 11.2 g of pyridine-N-oxide-2-thiol to give the title compound. The isolation of the product is carried out in an analogous manner. The yield of diphenoxy(2-pyridinethiolato)aluminum N-oxide is 22.5 g, about 75.4% of theory, of a fine white powder with a melting point of 233°-234.5° C.

| Microanalysis | % C | % H | % N | % S |
|---|---|---|---|---|
| Calculated | 60.17 | 4.16 | 4.13 | 9.45 |
| Found | 60.53 | 4.28 | 4.10 | 9.52 |

EXAMPLE 10

Bis(2-biphenylyloxy)(2-pyridinethiolato)aluminum N-oxide

In a manner analogous to that described in Example 1, 17.5 g of triisobutylaluminum and 30 g of 2-phenylphenol are reacted to give bis(2-biphenylyloxy)isobutylaluminum and this is then reacted with 11.2 g of pyridine-N-oxide-2-thiol to give the title compound. The isolation of the product is carried out in an analogous manner. The yield of bis-(2-biphenylyloxy)(2-pyridinethiolato)aluminum N-oxide is 30.25 g, about 69.9% of theory, of a white finely granular powder with a melting point of 219°–221° C.

| Microanalysis | % C | % H | % N | % S |
|---|---|---|---|---|
| Calculated | 70.86 | 4.51 | 2.85 | 6.52 |
| Found | 71.86 | 4.35 | 3.00 | 6.45 |

EXAMPLE 11

Bis(n-butylphosphonato)(2-pyridinethiolato)aluminum N-oxide

In a manner analogous to that described in Example 1, 12.9 g of triisobutylaluminum and 18.0 g of the mono-n-butyl ester of phosphorous acid are reacted to give bis-(n-butylphosphonato)isobutylaluminum and this is then reacted with 8.26 g of pyridine-N-oxide-2-thiol to give the title compound. The isolation of the product is carried out in an analogous manner. The yield of bis(n-butylphosphonato)(2-pyridinethiolato)aluminum N-oxide is 23.2 g, about 83.6% of theory, of a whitish powder with a melting point of 227°–232° C. (with decomposition).

| Microanalysis | % C | % H | % N | % S | % P |
|---|---|---|---|---|---|
| Calculated | 36.54 | 5.66 | 3.28 | 7.50 | 14.50 |
| Found | 35.51 | 5.32 | 3.43 | 7.79 | 14.19 |

EXAMPLE 12

(n-Butylphosphonato)bis(2-pyridinethiolato)aluminum N,N'-dioxide

In a manner analogous to that described in Example 1, 12.9 g of triisobutylaluminum and 8.98 g of the mono-n-butyl ester of phosphorous acid are reacted to give bis-(isobutyl)(n-butylphosphonato)aluminum and this is then reacted with 16.5 g of pyridine-N-oxide-2-thiol to give the title compound. The isolation of the product is carried out in an analogous manner. The yield of (n-butylphosphonato)bis(2-pyridinethiolato)aluminum N,N'-dioxide is 22.8 g, about 84.2% of theory, of yellowish crystals with a melting interval of 224°–228° C. (with decomposition).

| Microanalysis | % C | % H | % N | % S | % P |
|---|---|---|---|---|---|
| Calculated | 40.38 | 4.36 | 6.73 | 15.40 | 7.44 |
| Found | 39.21 | 4.16 | 6.86 | 15.84 | 6.86 |

EXAMPLE 13

Bis(ethylphosphonato)(2-pyridinethiolato)aluminum N-oxide

To 10 g of 98% diethyl phosphite at 0° C. are added dropwise 50 ml of 25% aqueous ammonia while stirring. The mixture is allowed to stir for an additional 1 hour at room temperature and the volatile constituents (ammonia, ethanol and water) are distilled off at 50° C. (bath temperature) and under reduced pressure. For the azeotropic removal of the water which is still present, the residue is treated twice with 100 ml of absolute toluene and each time the toluene is distilled off at 50° C. in vacuo. The contents of the reaction flask are dried for 24 hours at 50° C. in a high vacuum. The product consists of the ammonium salt of the monoethyl ester of phosphorous acid.

To the above flask contents are added 200 ml of absolute toluene and the resulting suspension is stirred for a half hour at 50° C. Thereafter, the reaction mixture is left to cool to room temperature and there is added dropwise thereto during 1 hour a solution of 5.5 g of isobutylaluminum dichloride in 70 ml of absolute toluene. The reaction mixture is warmed for 1 hour at 60° C., it is then allowed to cool to 20° C. and the precipitated ammonium chloride is filtered off with the exclusion of air and moisture. The ammonium chloride is rinsed twice with 10 ml of absolute toluene each time. To the combined filtrate is added dropwise within 1 hour at room temperature a solution of 4.5 g of pyridine-N-oxide-2-thiol in 50 ml of absolute toluene. The mixture is stirred for 1 hour at 40° C. and for 60 hours at room temperature. Thereby, the desired end product precipitates. The toluene is distilled off at 50° C. under reduced pressure and the product is rinsed twice with 25 ml of absolute n-hexane each time and subsequently dried for 12 hours in a high vacuum at 50° C. The yield of bis(ethylphosphonato)(2-pyridinethiolato)aluminum N-oxide is 11.3 g, about 86% of theory, as a yellowish crystallizate which melts at 208°–210° C. (with decomposition).

| Microanalysis | % C | % H | % N | % S |
|---|---|---|---|---|
| Calculated | 29.12 | 4.34 | 3.77 | 8.64 |
| Found | 29.76 | 4.48 | 3.97 | 8.86 |

EXAMPLE 14

(Ethylphosphonato)bis(2-pyridinethiolato)aluminum N,N'-dioxide

The sodium salt of the monoethyl ester of phosphorous acid is prepared from diethyl phosphite and sodium hydroxide in a manner analogous to that described in the first paragraph of Example 13. 2.72 g of this salt are reacted with 3.64 g of diisobutylaluminum chloride and 5.24 g of pyridine-N-oxide-2-thiol in a manner analogous to that described in the second paragraph of Example 13. In this manner the yield of (ethylphosphonato)bis(2-pyridinethiolato)aluminum N,N'-dioxide is 7.0 g, about 87.5% of theory, as a yellow-brownish crystallizate with a melting interval of 208°–220° C. (with decomposition).

| Microanalysis | % C | % H | % N | % S | % P |
|---|---|---|---|---|---|
| Calculated | 37.12 | 3.63 | 7.21 | 16.51 | 7.98 |

| -continued | | | | | |
|---|---|---|---|---|---|
| Microanalysis | % C | % H | % N | % S | % P |
| Found | 37.77 | 3.90 | 6.87 | 16.81 | 8.45 |

EXAMPLE 15

(Sorbato)bis(2-pyridinethiolato)aluminum N,N'-dioxide

In a manner analogous to that described in Example 1, 12.2 g of triisobutylaluminum and 6.9 g of sorbic acid are reacted in absolute toluene to give sorbato-diisobutyl aluminum and this is then reacted with 15.6 g of pyridine-N-oxide-2-thiol to give the title compound. The isolation of the product is carried out in an analogous manner. The white product thereby precipitates to yield 22.7 g, about 93% of theory, of (sorbato)bis(2-pyridinethiolato)aluminum N,N'-dioxide and melts upon heating from about 270° C. (with decomposition).

| Microanalysis | % C | % H | % N | % S |
|---|---|---|---|---|
| Calculated | 49.23 | 3.87 | 7.18 | 16.42 |
| Found | 49.45 | 3.80 | 6.99 | 16.46 |

EXAMPLE 16

Phenoxy-bis(2-pyridinethiolato)aluminum N,N'-dioxide

In a manner analogous to that described in Example 1, triisobutylaluminum and phenol are reacted in absolute toluene to give phenoxy-diisobutylaluminum and this is then reacted with pyridine-N-oxide-2-thiol to give the title compound. The isolation of the product is carried out in an analogous manner. The yield of phenoxy-bis(2-pyridinethiolato)aluminum N,N'-dioxide, a white solid, is 98% of theory. Melting point: 240°–241° C. (with decomposition).

| Microanalysis | % C | % H | % N | % S |
|---|---|---|---|---|
| Calculated | 51.61 | 3.52 | 7.52 | 17.22 |
| Found | 51.79 | 3.72 | 7.36 | 17.02 |

EXAMPLE 17

Pentachlorophenoxy-bis(2-pyridinethiolato)aluminum N,N'-dioxide

In a manner analogous to that described in Example 1, triisobutylaluminum and pentachlorophenol are reacted in absolute toluene to give pentachlorophenoxydiisobutyl-aluminum and this is then reacted with pyridine-N-oxide-2-thiol to give the title compound. The isolation of the product is carried out in an analogous manner. The yield of pentachlorophenoxy-bis(2-pyridinethiolato)aluminum N,N'-dioxide, a white solid, is 89% of theory. Melting point, 231°–232° C. (with decomposition).

| Microanalysis | % C | % H | % N | % Cl | % S |
|---|---|---|---|---|---|
| Calculated | 35.29 | 1.48 | 5.14 | 32.55 | 11.77 |
| Found | 35.43 | 1.67 | 5.18 | 32.19 | 12.01 |

II. Preparation of the pyridine-N-oxide-2-thiol starting material:

EXAMPLE 18

To a solution of 25 g of pyridine-N-oxide-2-thiol sodium salt (e.g. sodium Omadin ® from Olin Corp., Rochester, N.Y., U.S.A.) in 130 ml of deionised water is added slowly and with good stirring a solution of 9.65 ml of glacial acetic acid in 25 ml of deionized water. Thereby, the pyridine-N-oxide-2-thiol precipitates. This product is filtered off and is thereafter washed twice with 50 ml of ice-cold deionised water each time.

To the filtrate are added 2 ml of glacial acetic acid and the aqueous solution is subsequently extracted twice with 100 ml of diethyl ether each time. The combined ether phases are concentrated under reduced pressure and the filtered-off moist product is added to the residue. The water adhering to the product is thereafter removed azeotropically with absolute toluene by concentrating the solution twice with 25 ml of toluene each time at about 50° C. under reduced pressure or leaving the product to dry at about 35° C. under reduced pressure.

The yield of pyridine-N-oxide-2-thiol is 16 g, about 74.5% of theory, as a light grey-brown crystalline material which should be reacted as soon as possible to give the respective desired end products of formula I.

III. Formulation Examples

EXAMPLE 19

An anti-dandruff lotion has the following composition:

| 1000 ml contain | |
|---|---|
| (2-phenoxyethoxy)bis(2-pyridinethiolato)-aluminum N,N'—dioxide | 0.5 g |
| Rectified alcohol (94%) | 300.0 g |
| Cysteine hydrochloride | 1.0 g |
| D-Panthenol | 5.0 g |
| Citric acid (anhydrous) | 1.0 g |
| Triethanolamine (50 weight percent) | 7.6 g |
| Distilled or demineralized water ad | 1000 ml |

EXAMPLE 20

Foot-care composition (in the form of a lotion).

| 1000 ml contain a paste consisting of | |
|---|---|
| Cremophor ® RH 60 [solubilizing agent: hydrogenated castor oil/ethylene oxide (1:60) adduct] and | 2.0 g |
| (2-biphenylyloxy)bis(2-pyridinethiolato)-aluminum N,N'—dioxide | 0.5 g |
| Ethanol (94 weight percent) | 400 ml |
| d,l-α-Tocopherol | 0.1 g |
| Distilled water ad | 1000 ml |

The above-mentioned paste is prepared by melting the Cremophor ®RH 60, adding the aluminum compound and subsequently homogenizing the mixture. After dissolving the paste in the ethanol, the d,l-α-tocopherol and distilled water are then added.

EXAMPLE 21

Foot-care composition (in the form of a spray).

| | |
|---|---|
| Phenoxy-bis(2-pyridinethiolato)-aluminum N,N'—dioxide | 0.2 g |

| | |
|---|---|
| Methanol | 16.0 g |
| Distilled water | 24.0 g |
| Carrier gas (a 1:1 mixture of dichlorodifluoromethane and dichlorotetrafluoroethane) ad | 100.0 g |

EXAMPLE 22

An anti-dandruff shampoo has the following composition:

| | |
|---|---|
| Phosphoric acid disodium salt dihydrate | 31.35 g |
| Citric acid (anhydrous) | 2.50 g |
| Sodium lauryl ether sulphate (active washing substance 28%) | 400.00 g |
| D-Panthenol | 5.00 g |
| (1-Hexadecanolato)bis(2-pyridine-thiolato) aluminum N,N'—dioxide | 6.50 g |
| Perfume | 4.00 g |
| Distilled water ad | 1000.00 g |

IV. Biological Reports:

EXAMPLE 23

Activity against *Pityrosporum ovale* (dandruff)

Solutions of the compounds to be tested in various concentrations are added to a nutrient medium. Water or polyethyleneglycol is used as the solvent. The surface of the nutrient medium is streaked with a suspension of *Pityrosporum ovale* Strain No. 1 and incubated at 25° C. After 5 days, the growth of the yeast is examined with the naked eye. The results are recorded in the following Table.

TABLE

| Compound (Example No.) | Concentration (μg/ml), at which growth is still ascertained | Concentration (μg/ml), at which growth is no longer ascertained |
|---|---|---|
| (2-Phenoxyethoxy)bis-(2-pyridinethiolato)-aluminum N,N'—dioxide (8) | 0.1 | 1 |
| Bis(ethylphosphonato)(2-pyridinethiolato)-aluminum N—oxide (13) | 0.1 | 1 |
| (Ethylphosphonato)bis(2-pyridinethiolato)-aluminum N,N'—dioxide (14) | 1 | 10 |
| (2-Biphenylyloxy)bis(2-pyridinethiolato)-aluminum N,N'—dioxide (2) | 1 | 10 |
| (Sorbato)bis(2-pyridine-thiolato)aluminum N,N'—dioxide (15) | 1 | 10 |
| Hexachlorophene — State of the art | 10 | 100 |
| Tri(2-pyridine-thiolato)-aluminum — State of the art | 1 | 10 |

I claim:

1. A compound of the formula

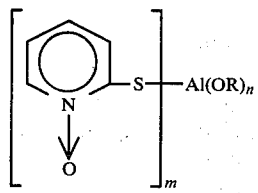

wherein
m is 1 or 2,
n is 1 or 2,
whereby the sum m+n is 3, and
R is ethyl or n-hexadecyl; straight-chain or branched $C_{1-4}$-alkyl monosubstituted with phenoxy; 2,4-hexadienoyl; unsubstituted phenyl or phenyl substituted with 1 to 5 chlorine atoms or a phenyl group; or a group of the formula

  (a)

wherein
$R^1$ is $C_{1-6}$-alkyl, or,
where m is 1 and n is 2, the two R-symbols together form a 2,2'-methylene-bis-(3,4,6-trichloro-o-phenylene)group, or,
where m is 2 and n is 1, R is a 2,4,5-trichloro-6-[2,3,5-trichloro-6-[di(2-pyridinethiolato)aluminum]oxybenzyl]phenyl N,N'-dioxide group.

2. A compound according to claim 1, wherein R is straight-chain or branched $C_{1-4}$-alkyl monosubstituted with phenoxy, 2,4-hexadienoyl, optionally substituted phenyl, a group of formula (a) or the 2,4,5-trichloro-6-[2,3,5-trichloro-6-[di(2-pyridinethiolato)aluminum]oxybenzyl]phenyl N,N'-dioxide group.

3. A compound according to claim 1 or 2, wherein m is 1 and n is 2.

4. A compound according to claim 1, (2-phenoxyethoxy)bis(2-pyridinethiolato)aluminum N,N'-dioxide.

5. A compound according to claim 1, bis(ethylphosphonato)(2-pyridinethiolato)aluminum N-oxide.

6. A compound according to claim 1, (2-biphenylyloxy)bis(2-pyridinethiolato)aluminum N,N'-dioxide.

7. A compound according to claim 1, [methylene-bis(3,4,6-trichloro-o-phenyleneoxy)]bis[(di-2-pyridinethiolato)]aluminum N,N', N'', N'''-tetroxide.

8. A compound according to claim 1, selected from the group consisting of:
Ethoxy-bis(2-pyridinethiolato)aluminum N,N'-dioxide,
(2,4,6-trichlorophenoxy)bis(2-pyridinethiolato)aluminum N,N'-dioxide,
(1-hexadecanolato)bis(2-pyridinethiolato)aluminum N,N'dioxide,
[methylene-bis(3,4,6-trichloro-o-phenyleneoxy)](2-pyridinethiolato)aluminum N-oxide,
Bis(2-phenoxyethoxy)(2-pyridinethiolato)aluminum N-oxide,
diphenoxy(2-pyridinethiolato)aluminum N-oxide,
bis(2-biphenylyloxy)(2-pyridinethiolato)aluminum N-oxide,
bis(n-butylphosphonato)(2-pyridinethiolato)aluminum N-oxide, (n-butylphosphonato)bis(2-pyridinethiolato)aluminum N,N'-dioxide, (ethylphosphonato)bis(2-pyridinethiolato)aluminum N,N'-dioxide, (sorbato)bis(2-pyridinethiolato)aluminum N,N'-dioxide, phenoxy-bis(2-pyridinethiolato)aluminum N,N'-dioxide and pentachlorophenoxy-bis(2-pyridinethiolato)aluminum N,N'-dioxide.

9. An antimicrobial cosmetic composition, comprising a cosmetic base and an antimicrobially-effective amount of at least one compound of the formula

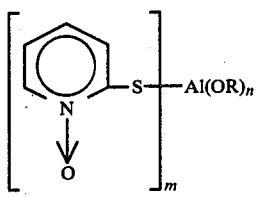

wherein m is 1 or 2, n is 1 or 2, whereby the sum m+n is 3, and

R is ethyl or n-hexadecyl; straight-chain or branched $C_{1-4}$-alkyl monosubstituted with phenoxy; 2,4-hexadienoyl; unsubstituted phenyl or phenyl substituted with 1 to 5 chlorine atoms or a phenyl group; or a group of the formula

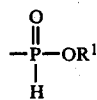

(a)

wherein $R^1$ is $C_{1-6}$-alkyl, or, where m is 1 and n is 2, the two R-symbols together form a 2,2'-methylene-bis(3,4,6-trichloro-o-phenylene) group, or, where m is 2 and n is 1, R is a 2,4,5-trichloro-6-[2,3,5-trichloro-6-[di(2-pyridinethiolato)aluminum]oxybenzyl]phenyl N,N'-dioxide group.

10. The antimicrobial cosmetic composition according to claim 9, comprising an antimicrobially-effective amount of (2-phenoxyethoxy)bis(2-pyridinethiolato)aluminum N,N'-dioxide.

11. An antimicrobial cosmetic composition according to claim 9, comprising an antimicrobially-effective amount of bis(ethylphosphonato)(2-pyridinethiolato)aluminum N-oxide.

12. An antimicrobial cosmetic composition according to claim 9, comprising an antimicrobially-effective amount of (2-biphenylyloxy)bis(2-pyridinethiolato)aluminum N,N'-dioxide.

13. An antimicrobial cosmetic composition according to claim 9, comprising an antimicrobially-effective amount of [methylene-bis(3,4,6-trichloro-o-phenyleneoxy)]bis[(di-2-pyridinethiolato)]aluminum N,N', N'', N'''-tetroxide.

14. A method for the control or prevention of dandruff of the scalp, which comprises treating the scalp with an effective amount of the cosmetic composition according to claim 9.

15. A method for the control or prevention of dandruff of the scalp, which comprises treating the scalp with an effective amount of the cosmetic composition according to claim 10.

16. A method for the control or prevention of dandruff of the scalp, which comprises treating the scalp with an effective amount of the cosmetic composition according to claim 11.

17. A method for the control or prevention of dandruff of the scalp, which comprises treating the scalp with an effective amount of the cosmetic composition according to claim 12.

18. A method for the control or prevention of dandruff of the scalp, which comprises treating the scalp with an effective amount of the cosmetic composition according to claim 13.

* * * * *